United States Patent
Zacharie et al.

(10) Patent No.: US 8,080,555 B2
(45) Date of Patent: Dec. 20, 2011

(54) PURINE DERIVATIVES AND THEIR USE FOR TREATMENT OF AUTOIMMUNE DISEASES

(75) Inventors: Boulos Zacharie, Laval (CA); Daniel Fortin, Rosemère (CA); Nicole Wilb, Montreal (CA); Christopher Penney, Pierrefonds (CA)

(73) Assignee: Prometic Biosciences Inc., Laval, Quebec (CA)

( * ) Notice: Subject to any disclaimer, the term of this patent is extended or adjusted under 35 U.S.C. 154(b) by 846 days.

(21) Appl. No.: 11/919,990

(22) PCT Filed: May 15, 2006

(86) PCT No.: PCT/CA2006/000783
§ 371 (c)(1),
(2), (4) Date: Nov. 6, 2007

(87) PCT Pub. No.: WO2006/136005
PCT Pub. Date: Dec. 28, 2006

(65) Prior Publication Data
US 2009/0042768 A1    Feb. 12, 2009

Related U.S. Application Data

(60) Provisional application No. 60/681,141, filed on May 16, 2005.

(51) Int. Cl.
C07D 473/16 (2006.01)
C07D 473/40 (2006.01)
C07D 473/34 (2006.01)
A61K 31/52 (2006.01)
C07K 1/10 (2006.01)
G01N 33/53 (2006.01)

(52) U.S. Cl. ...... 514/263.4; 435/7.1; 530/413; 544/277; 544/264

(58) Field of Classification Search .......... 544/277; 514/263.4; 530/413
See application file for complete search history.

(56) References Cited

U.S. PATENT DOCUMENTS

| | | | |
|---|---|---|---|
| 6,790,958 B2 * | 9/2004 | Lum et al. | 544/277 |
| 6,949,644 B2 | 9/2005 | Ding et al. | |
| 7,176,312 B2 | 2/2007 | Ding et al. | |
| 2003/0171583 A1 | 9/2003 | Ding et al. | |
| 2003/0191312 A1 | 10/2003 | Ding et al. | |
| 2005/0124637 A1 * | 6/2005 | Cheng et al. | 514/263.2 |
| 2006/0009642 A1 | 1/2006 | Ding et al. | |
| 2006/0293330 A1 * | 12/2006 | Janssen et al. | 514/248 |
| 2007/0191380 A1 | 8/2007 | Ding et al. | |
| 2007/0197559 A1 * | 8/2007 | Bakthavatchalam et al. | 514/261.1 |

FOREIGN PATENT DOCUMENTS

| CA | 2463507 | 4/2003 |
|---|---|---|
| WO | WO 2005/0844101 | 9/2005 |

OTHER PUBLICATIONS

El-Bayouki, Egyptian Journal of Chemistry (1991), Volume Date 1990, 33(3), 243-53.*
Holers, J. Clin. Invest. 114(5):616-619, 2004.*
Kelly et al. "Substituted-(3-formamidobenzyl)-9H-purines. Benzodiazepine receptor binding activity" STN database CAPLUS Doc. No. 115: 183232, Accession No. 1991:583232, *Journal of Heterocyclic Chemistry* (1991), vol. 28, No. 4, pp. 1099-1104.
Kelly et al. "6-(Alkylamino)-9-benzyl-(H-purines. A new class of anticonvulsant agents" STN database CAPLUS Doc. No. 108:94501, Accession No. 1988:94501, *Journal of Medicinal Chemistry* (1988), vol. 31, No. 3, pp. 606-612.
Tsuyoshi et al. "Recent advances in the treatment of graft-versus-host disease" *Clinical Medicine & Research*, Oct. 2004, vol. 2, No. 4, pp. 243-252.
International Search Report for PCT/CA2006/000783 completed Jul. 24, 2006, four pages.
Written Opinion PCT/CA2006/000783 completed Jul. 24, 2006, five pages.

* cited by examiner

*Primary Examiner* — Mark Berch
(74) *Attorney, Agent, or Firm* — Clark & Elbing LLP

(57) ABSTRACT

Compounds useful in the treatment of autoimmune disease are described by the following general formula:

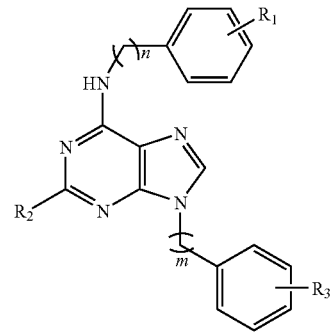

n=0-2
m=0-2
m is not necessarily equal to n;
where $R_1$, $R_3$=$NH_2$, F, Cl, $C_1$-$C_4$ alkoxy or phenoxy group, but $R_1$ is not necessarily equal to $R_3$; and
$R_2$=H, F, Cl, $NH_2$, or NH—R—XH;

where R = —$(CH_2)_p$—
p = 2-4

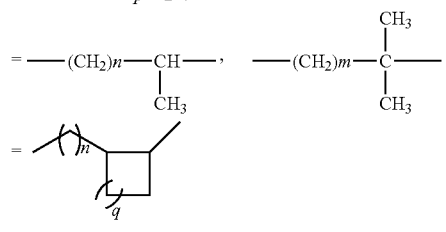

q = 0-3
X = $CH_2$, NH, O, or S.

15 Claims, 2 Drawing Sheets

PURINE DERIVATIVES AND THEIR USE FOR TREATMENT OF AUTOIMMUNE DISEASES

CROSS-REFERENCE TO RELATED APPLICATION

This application claims the benefit of provisional U.S. Appln. No. 60/681,141, filed May 16, 2005.

FIELD OF THE INVENTION

The present invention comprises new compounds described by the following general formula:

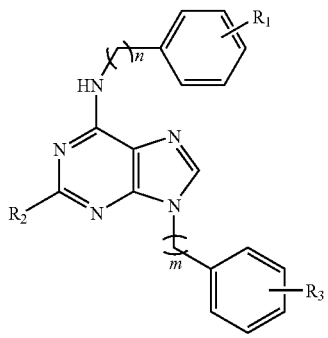

n=0-2
m=0-2
m is not necessarily equal to n;
where $R_1$, $R_3$=$NH_2$, F, Cl, $C_1$-$C_4$ alkoxy or phenoxy group, but $R_1$ is not necessarily equal to $R_3$; and
$R_2$=H, F, Cl, $NH_2$, or NH—R—XH;

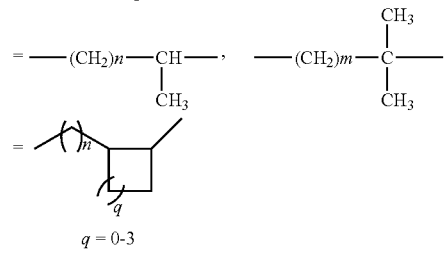

X = $CH_2$, NH, O, or S

These compounds are useful in that they may be used for the treatment of autoimmune diseases.

BACKGROUND OF THE INVENTION

Autoimmune disease refers to any of a group of diseases or disorders in which tissue injury is associated with a humoral and/or cell-mediated immune response to body constituents or, in a broader sense, an immune response to self. The pathological immune response may be systemic or organ specific. That is, for example, the immune response directed to self may affect joints, skin, the myelin sheath that protects neurons, kidney, liver, pancreas, thyroid, adrenals, and ovaries. In fact, the list of autoimmune diseases is composed of more than eighty disorders. A few autoimmune diseases such as vitiligo, in which patches of skin lose pigmentation, are merely annoying. Most others are debilitating, often progressive with time and eventually fatal. Systemic lupus erythematosus (SLE), for example, is a chronic disease in which 10-15% of patients die within a decade of diagnosis. In all but a few autoimmune diseases, the sex ratio skews towards women. For example, in SLE the ratio of female to male patients is nine to one. In one particular case, Hashimoto's disease in which the immune system attacks the thyroid gland, the ratio is fifty to one.

It has long been known that immune complex formation plays a role in the etiology and progression of autoimmune disease. For example, in Goodman and Gilman's *The Pharmacological Basis of Therapeutics*, 16th Edition (1980), Macmillan Publishing Co., on page 683, inflammation in patients with arthritis is stated to probably involve phagocytosis by leukocytes of complexes of antigen, antibody and complement—immune complexes. However, only now it is being recognized that inflammation caused by immune complexes in the joints (arthritis), the kidneys (glomerulonephritis), and blood vessels (vasculitis) is a major cause of morbidity in autoimmune diseases as noted by Hogarth, P. M., et al., *Annual Reports in Medicinal Chemistry* 37:17-224 (2002). Increased immune complex formation correlates with the presence of antibodies directed to self or so-called autoantibodies, and the presence of the latter can also contribute to tissue inflammation either as part of an immune complex or unbound to antigen (free antibody). In some autoimmune diseases, the presence of free autoantibody contributes significantly to disease pathology. This has been clearly demonstrated for example, in SLE (anti-DNA antibodies), ITP (antibody response directed to platelets), and to a lesser extent rheumatoid arthritis (IgG reactive rheumatoid factor). The important role of immune complexes and free autoantibodies is further demonstrated by the fact that successful treatment of certain autoimmune diseases has been achieved by the removal of immune complexes and free antibody by means of specific immunoadsorption procedures. For example, the use of an apheresis procedure in which immune complexes and antibodies are removed by passage of a patient's blood through an immunoaffinity (PROSORBA®) column was approved by the U.S. FDA in 1987 for immune thrombocytopenia (ITP) and in 1999 for rheumatoid arthritis. However, currently there is no approved method for the treatment of autoimmune diseases which facilitates the elimination of immune complexes and autoantibodies by administration of a drug.

Another aspect of the etiology and progression of autoimmune disease is the role of proinflammatory cytokines. Under normal circumstances, proinflammatory cytokines such as tumor necrosis factor α (TNFα) and interleukin-1 (IL-1) play a protective role in the response to infection and cellular stress. However, the pathological consequences which result from chronic and/or excessive production of TNFα and IL-1 are believed to underlie the progression of many autoimmune diseases such as rheumatoid arthritis, Crohn's disease, inflammatory bowel disease, and psoriasis. Other proinflammatory cytokines include interleukin-6, interleukin-8, interleukin-17, and granulocyte-macrophage colony stimulating factor. However, it appears that TNFα is on the top of the proinflammatory cytokine cascade. That is, in terms of blocking one proinflammatory cytokine, blockage of TNFα would provide the maximum therapeutic effect. The ability of TNFα to downregulate other proinflammatory cytokines is reviewed by Feldmann, M., in *Perspectives* 2:364-371 (2002). Indeed, the impact of the antagonism of TNFα as a treatment option for arthritis, psoriatic arthritis, psoriasis, and Crohn's disease has been illustrated by the U.S. FDA approval of REMICADE® (chimeric anti-TNFα monoclonal antibody), ENBREL® (soluble TNFα p75 receptor fusion protein), and HUMIRA® (human anti-TNFα monoclonal antibody).

As may be inferred from the above discussion regarding the etiology and progression of autoimmune disease, its pathogenesis is complex and multifactorial. As such, there is a multitude of therapies available. However, the majority of autoimmune diseases are poorly controlled by conventional treatments. Prior art treatments are not uniformly effective and are often associated with moderate to severe toxicity. Nonetheless, the above discussion indicates that there is a need for simple, well-defined organic compounds which can help the body eliminate immune complexes or at least prevent the deposition of circulating immune complexes and/or (simultaneously) inhibit the activity of TNFα while still being well-tolerated by the patient. In summary, there is a need for an efficacious yet well-tolerated treatment of chronic autoimmune disease.

The present invention provides compounds that are useful for the treatment of chronic autoimmune disease. Although not initially life-threatening, most autoimmune diseases are chronic conditions which slowly progress to a debilitating state. While numerous therapies are available, conventional treatments are not routinely efficacious. More problematic is the accompanying toxicity which often prohibits the long-term use necessary with a chronic disease. Current treatments for autoimmune disease can be broadly classified into two groups: those drugs which dampen or suppress the immune response to self and those drugs which address the symptoms that arise from chronic inflammation. In greater detail, conventional treatments for autoimmune disease (e.g., primarily arthritis) are as follows:

1. Nonsteroidal Anti-Inflammatory Drugs (NSAIDs): These include aspirin, ibuprofen, naproxen, etodolac, and ketoprofen. NSAIDs are not relatively potent drugs and so are most commonly used as anti-inflammatory drugs in the early stages of disease (e.g., to relieve the pain and swelling which accompanies arthritis). However, NSAIDs are associated with gastrointestinal irritation and liver toxicity. In order to address the gastrointestinal ulceration associated with the use of many NSAIDs, more selective NSAID drugs have been recently developed which selectively inhibit (VIOXX®, CELEBREX®) or preferentially inhibit (MOBICOX®) cyclooxygenase-2 (i.e., COX-2 inhibitors). However, COX-2 inhibitors display untoward side effects which include gastrointestinal irritation, especially with longer-term use.

2. Corticosteroids: These include prednisone and dexamethasone. Corticosteroids are the most widely used anti-inflammatory agents for the treatment of rheumatoid arthritis. However, they significantly increase the risk of osteoporosis, gastrointestinal toxicity, and infection arising from generalized immune suppression. Therefore, corticosteroids tend to be used for the treatment of disease flares (e.g., SLE) and not as a chronic treatment.

3. Disease-Modifying Anti-Rheumatic Drugs (DMARDs): These include cytotoxic drugs such as methotrexate, azathioprine, and cyclophosphamide; potent immunosuppressants such as cyclosporin A (SANDIMMUNE®, NEORAL®) and FK506 (tacrolimus); and a variety of other drugs such as hydrochloroquine and organogold salts (e.g., aurothioglucose). DMARDs are potent drugs and so can display significant efficacy in reducing inflammation and slowing the rate of disease progression. As such, physicians have traditionally used DMARDs as a second line of therapy after NSAIDs. However, as potent drugs, DMARDs have significant toxicity associated with their use. Cytotoxic drugs, for example, interfere with DNA replication which manifests itself with a number of toxic effects. The latter include bone marrow depression and subsequent risk of infection and neoplasia. The use of cyclosporin A and FK506 is limited by serious side effects which include renal and liver toxicities. Toxic effects associated with the use of hydrochloroquine include blindness, neuromyopathy, and gastrointestinal distress. The most common side effect arising from therapy with gold salts is dermatitis. However, gold toxicity can cause nephritis and bone marrow depression.

4. Biologicals: These include the recombinant proteins REMICADE®, ENBREL®, and HUMIRA®, all of which target TNFα, KINERET®, which targets interleukin-1, Amevive which targets T-cells (CD2 surface glycoprotein) and RAPTIVA® which also targets T-cells (anti-CD11a antibody). However, recombinant proteins and in particular recombinant antibodies are difficult to produce for widespread use and have toxic side effects associated with their use. Toxicities include potential immunological reactions, especially with the prolonged use that may be required for chronic conditions. In addition to the well-known HAMA (human anti-mouse antibody) response associated with chimeric or humanized antibodies, antibody mediated cytotoxicity mechanisms (ADCC and complement-mediated) may lead to side effects. More recently, it was discovered that antibodies, regardless of source or antigen specificity, can convert molecular oxygen into hydrogen peroxide and ozone as described by Wentworth, P., et al. *Science* 293:1806-1811 (2001) and 298:2195-2199 (2002).

This could lead to cellular and tissue damage which may exacerbate treatment of an autoimmune condition with prolonged use. For example, it was shown that the production of hydrogen peroxide and ozone by antibodies could be linked to an inflammatory response in rats: the so-called Arthus reaction. The potent anti-TNFα activity of the REMICADE® antibody has led to increased risk of opportunistic infections which include tuberculosis, histoplasmosis, listeriosis, and pneumocytosis.

SUMMARY OF THE INVENTION

It is an objective of the present invention to provide novel compounds for use in treating autoimmune disease. An autoimmune disease, in particular chronic conditions like arthritis and SLE, may be treated by administration of a compound as described herein to a mammal, preferably a human. Therefore, in accordance with this invention, di- or trisubstituted purines and their pharmaceutical compositions are provided which are able to facilitate the clearance of immune complexes or limit their deposition within body organs such as kidney and/or to inhibit the proinflammatory actions of TNFα.

In one embodiment of the present invention, these purine compounds will affect both aspects of the inflammation process: immune complexes and TNFα. The therapeutic benefit resulting from this dual mechanism of action will manifest itself in terms of an improved toxicity profile. That is, the purine compounds described in this invention are not potent inhibitors of TNFα nor will they completely eliminate immune complexes. TNFα does play a role in protection against infection while immune complexes play a role in feedback mechanisms regulating immune response (so-called idiopathic determinants). Therapeutic efficacy may result from the additive effect of the two mechanisms of action. Furthermore, toxicity due to chronic treatment and/or other drugs used in combination may be at least reduced or avoided.

In another embodiment of the present invention, the purine compounds will affect only one aspect of the inflammation process. That is, these compounds will affect either immune complexes or TNFα. In the case where the purine compounds influence the elimination of immune complexes or prevent their deposition, such compounds are expected to be particularly useful for the treatment of arthritis, systemic lupus erythematosus (SLE), immune thrombocytopenia (ITP), glomerulonephritis, and vasculitis. In the case where the purine compounds inhibit TNFα, such compounds are expected to be particularly useful for the treatment of rheumatoid arthritis, psoriatic arthritis, psoriasis, Crohn's disease, inflammatory bowel disease, ankylosing spondylitis, Sjögren's syndrome, Still's disease (macrophage activation syndrome), uveitis, scleroderma, myositis, Reiter's syndrome, and Wegener's syndrome. Of course, it is possible that some purine compounds of this invention will affect the inflammation process by a biochemical mechanism which is in addition to and distinct from an effect on immune complexes and/or TNFα. One such possible alternative mechanism, for example, by virtue of the purine scaffold, is an effect on adenosine receptors. However, regardless of the mechanism(s) by which the purine compounds affect the targeted autoimmune disease, it is an important aspect of this invention that said compounds do not potently affect any aspect of the inflammation process such that treatment is well tolerated.

Further aspects of the invention will be apparent to a person skilled in the art from the following description and claims, and generalizations thereto.

DETAILED DESCRIPTION OF CERTAIN EMBODIMENTS OF THE INVENTION

Figure 1:
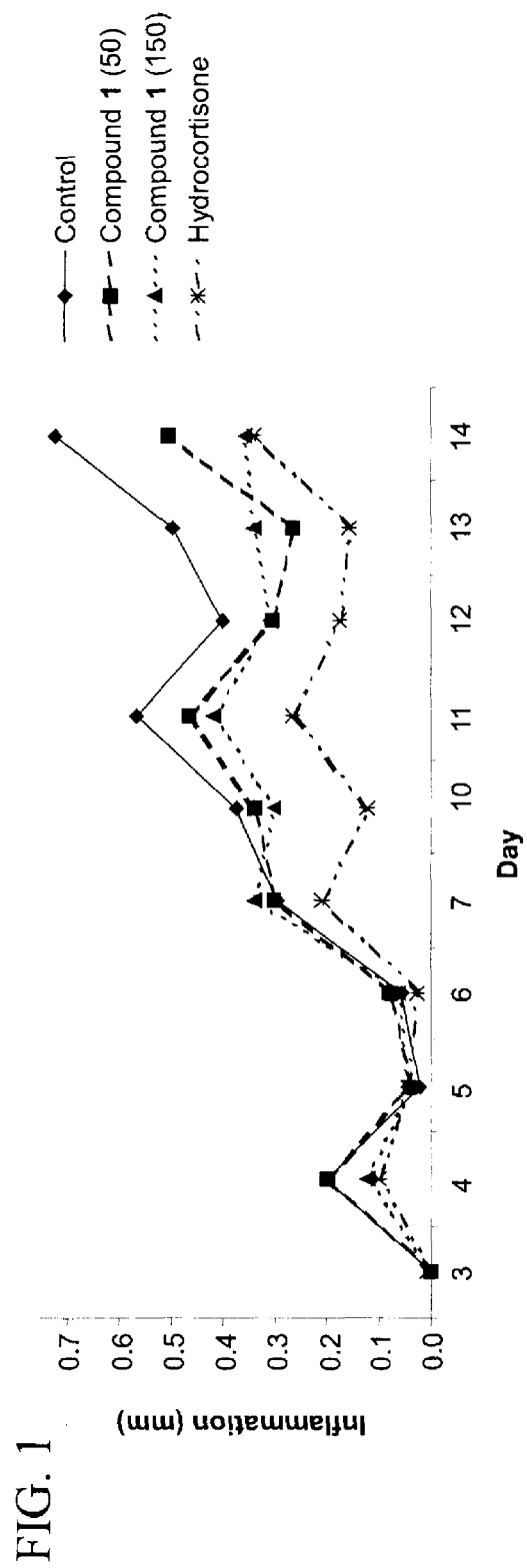
FIG. 1 shows the effect of oral administration of compound 1 as compared to hydrocortisone on delayed-type hypersensitivity (DTH).

The present invention includes compounds, or pharmaceutically acceptable derivatives thereof, of the following general formula:

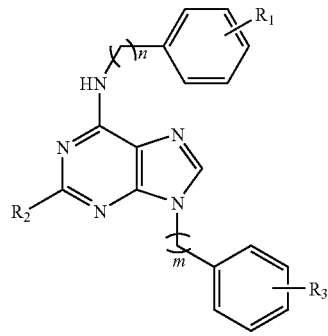

$n = 0\text{-}2$
$m = 0\text{-}2$
m is not necessarily equal to n;
where $R_1$, $R_3 = NH_2$, F, Cl, $C_1$-$C_4$ alkoxy or phenoxy group, but $R_1$ is not necessarily equal to $R_3$; and
$R_2 = H$, F, Cl, $NH_2$, or NH—R—XH;

where R = —(CH$_2$)$_p$—
$p = 2\text{-}4$

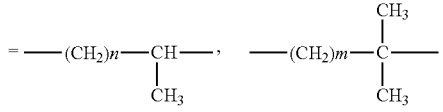

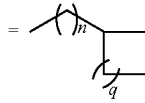

$q = 0\text{-}3$
X = CH$_2$, NH, O, or S

It is a preferred embodiment of the present invention that n≠m (e.g., n=0, m=2), $R_1$=NH$_2$, $R_3$=NH$_2$, F or Cl, or any combination thereof. More preferred is when $R_1$=meta-NH$_2$, F or Cl.

Particularly preferred are the following compounds:

| Compound No. | Structure |
|---|---|
| 1 | 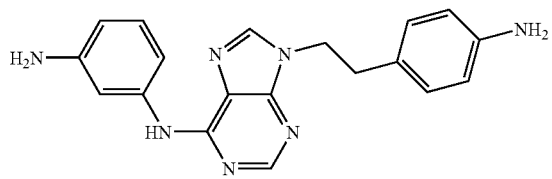 |

-continued
| Compound No. | Structure |
| --- | --- |
| 2 | 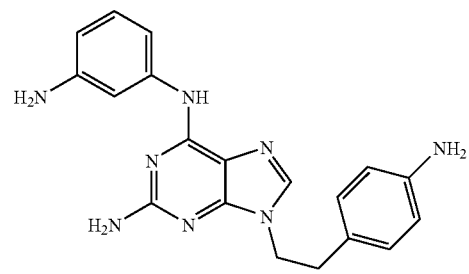 |
| 3 | 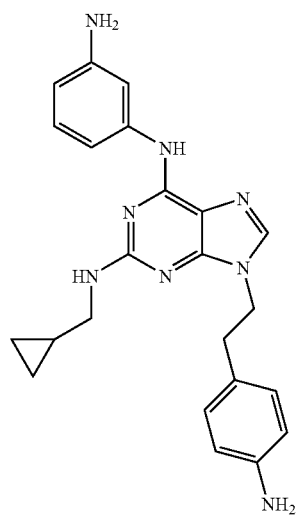 |
| 4 | 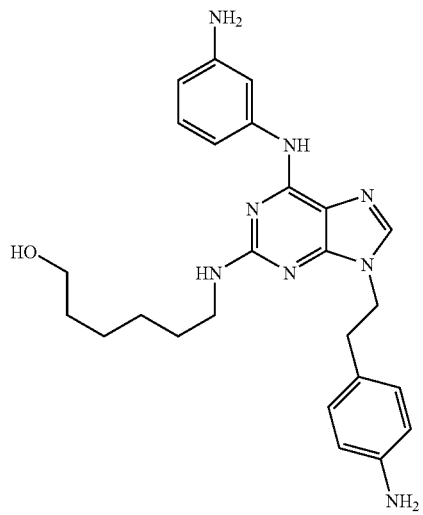 |

-continued
| Compound No. | Structure |
|---|---|
| 5 | 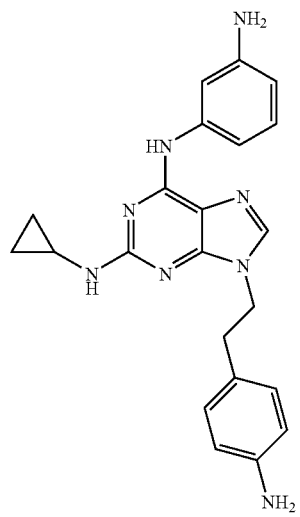 |
| 6 | 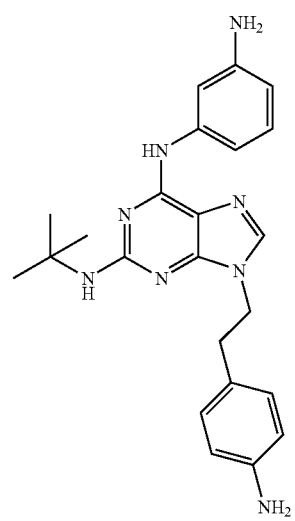 |
| 7 | 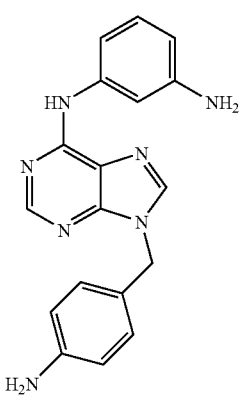 |

-continued
| Compound No. | Structure |
|---|---|
| 8 | 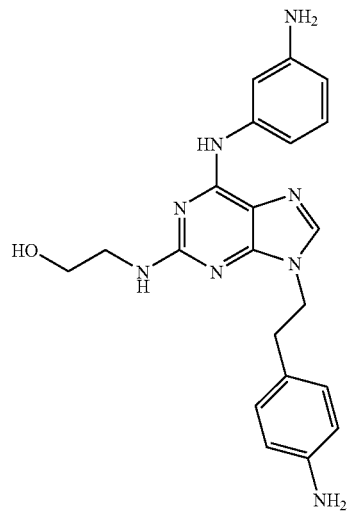 |
| 9 | 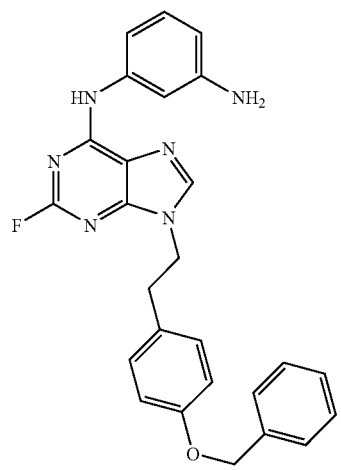 |
| 10 | 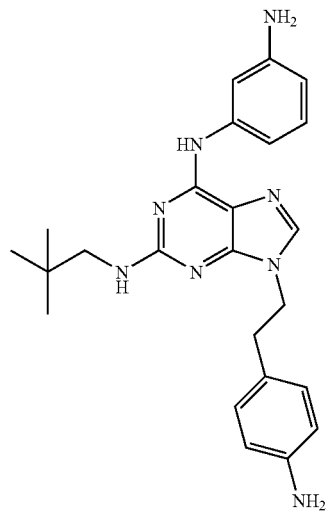 |

-continued
| Compound No. | Structure |
| --- | --- |
| 11 | 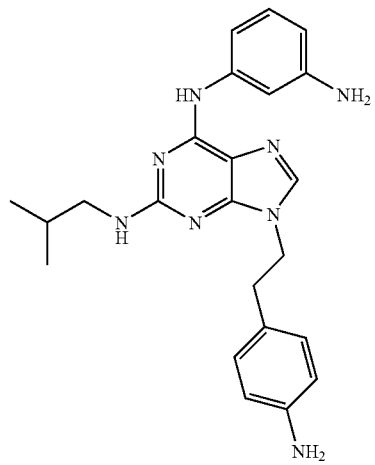 |
| 12 | 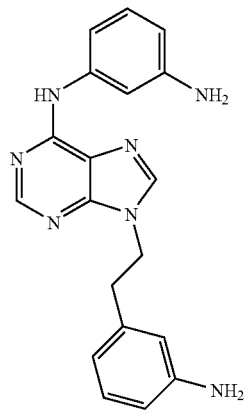 |
| 13 | 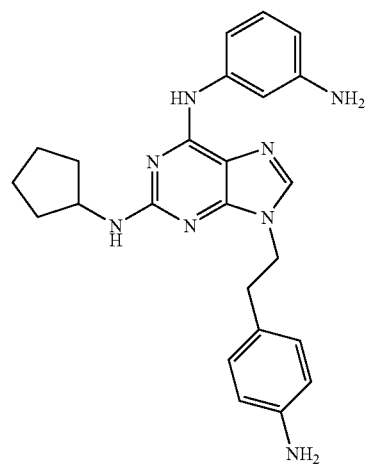 |

-continued

| Compound No. | Structure |
|---|---|
| and 14 | 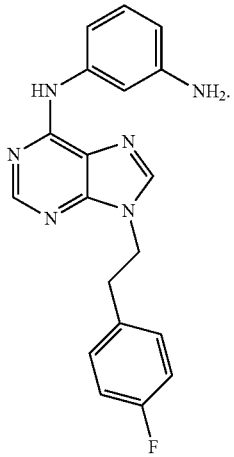 |

Compounds of the present invention may facilitate the clearance of immune complexes by phagocytosis or may limit the deposition of complexes within body organs and tissues by their ability to antagonize the binding of immune complexes to organ and tissue surfaces. The mechanism by which immune complexes attach to various surfaces can involve binding to cell-surface Fc receptors. Fc receptors are glycoproteins of inflammatory leukocytes that bind the Fc (tail) portion of immunoglobulins. Fc receptors are also present on numerous tissues and provide a site for attachment and subsequent deposition of immune complexes onto tissue surfaces. For example, the deposition on kidney tissue of autoantibody containing complexes by binding to Fc receptors is thought to trigger an inflammatory response typical of SLE which can lead to glomerulonephritis. Well-characterized Fc receptors include: FcγRI, FcγRII, and FcγRIII (IgG receptors); FcεRI (the IgE receptor); and FcαRI (the IgA receptor). Interestingly, *Staphylococcal aureus* protein A is a cell-surface bacterial protein which can bind to the Fc (tail) portion of most antibodies. For example, protein A will bind to human IgG1, IgG2, and IgG4 immunoglobulins. More importantly, it has been known for many years that protein A can inhibit the binding of IgG antibody containing immune complexes to Fc receptors. For example, Sulica, A., et al. *Immunology* 38:173-179 (1979) reported that protein A does inhibit IgG containing immune complex binding to Fc receptors but protein A enhances binding of IgG to lymphocytes and macrophages.

More recently, with the availability of Fc receptor (γ chain) deficient mice, it became possible to establish the primary role of the IgG Fc receptors (FcγR) in mediating the effector responses seen in autoimmune diseases such as SLE and rheumatoid arthritis, as noted by Marino, M., et al. *Nature Biotechnology* 18:735-739 (2000). More specifically, these authors stated that agents which can interfere with the binding of immune complexes to FcγR should ameliorate SLE. They provided experimental support for this statement by treating a special strain of mice (MRL/lpr) that develops a syndrome which is similar to human SLE with a peptide which binds to the Fc portion of IgG. The survival rate of treated animals (80%) was significantly greater than untreated animals (10%). In a recent review article by Hogarth, P. M., *Current Opinion in Immunology* 14:798-802 (2002), it was stated that FcγR acts early in the inflammation process and engagement by immune complexes is a potent signal for the release of proinflammatory cytokines such as TNFα. In those cases where compounds of the present invention affect some aspect of immune complex clearance or deposition, they may do so by their ability to mimic protein A. That is, such compounds can bind to the Fc portion of human IgG as ascertained by their ability to inhibit the binding of protein A to human IgG, as determined in vitro by competitive ELISA. By binding to the Fc portion of human IgG in a fashion similar to protein A, such protein A mimic compounds may disrupt the binding of IgG containing immune complexes to FcγR. Subsequently, this should prevent deposition of immune complexes and thereby facilitate their clearance as well as diminish the release of proinflammatory cytokines.

Additionally, or alternatively, compounds of the present invention may inhibit the proinflammatory activity of TNFα. Unlike currently approved recombinant anti-TNFα monoclonal antibodies (REMICADE®, HUMIRA®) or soluble TNFα receptor (ENBREL®), compounds of the present invention do not inhibit the binding of TNFα to the p55 TNFα receptor (CD120a) or the p75 TNFα receptor (CD120b). Nonetheless, compounds of the present invention may inhibit the effect of TNFα as ascertained by their ability to inhibit TNFα induced apoptosis/cytotoxicity in the WEHI 164 (13var) murine cell line. Additionally, compounds of the present invention may inhibit the production of TNFα, as ascertained by their ability to inhibit LPS induced production of TNFα in the J774A-1 murine cell line.

TNFα is produced by many cell types which include fibroblasts and numerous immune cell subsets. Examples of the latter include macrophages, monocytes, B and T cells, and mast cells. It is a pleiotropic molecule produced in response to a variety of stimuli and which can exert effects on most cell types. Under normal circumstances, low levels of serum TNFα confer protection against pathogens, tumors, and tissue damage. Therefore, in terms of chronic or continued use of compounds of the present invention as therapeutic agents, it is one aspect of this invention that these compounds are not potent inhibitors of the effects or production of TNFα, nor do they potently inhibit the binding of TNFα to its receptor. The potential for long-term use of compounds of this invention is demonstrated by the treatment of NZBW/F1 mice (another model for human SLE) with compounds for approximately one year without observation of any significant toxicity.

Similar to biologicals described above, other TNFα inhibitors display toxicity which limits long-term or chronic use. For example, thalidomide (N-phthalimido-glutarimide) is a synthetic anti-inflammatory drug which inhibits TNFα synthesis. However, clinical trials for patients with rheumatoid arthritis have been mostly unsuccessful because of unacceptable toxicity. Severe side effects included somnolence, peripheral neuropathy, and severe rash. Many drugs that are commonly used as immunosuppressants such as cyclosporin A and methotrexate show TNFα inhibitory properties but also cannot be used on a chronic basis because of their toxicity.

Indeed, the pivotal role played by TNFα in many autoimmune diseases, as evidenced by the therapeutic success of recently approved biologicals along with the lack of efficacious yet nontoxic drugs available for chronic treatment, has led to the investigation of a number of approaches for the inhibition of TNFα. Approaches have included the search for inhibitors of phosphodiesterase IV, agonists of adenosine, matrix metalloproteinase inhibitors (e.g., inhibitors of TACE), signal transduction inhibitors (e.g., p38 MAP kinase), and inhibitors of transcription factors (e.g., NFκB). Clearly then, a need exists for compounds which can efficaciously inhibit the effects of TNFα but which can be used on a long-term basis for the treatment of chronic autoimmune diseases.

The present invention provides novel compounds as defined by the general formula above which are useful for the treatment of chronic autoimmune disease. These compounds may facilitate the clearance of immune complexes by phagocytosis or may limit the deposition of immune complexes within body organs and tissues by their ability to antagonize the binding of immune complexes to organ and tissue surfaces. In this case, such compounds may be particularly useful for the treatment of those autoimmune diseases where immune complexes play an important role in disease pathology: e.g., arthritis, SLE, ITP, glomerulonephritis, and vasculitis. Additionally, the compounds of this invention may inhibit the proinflammatory actions of TNFα. In this case, such compounds may be particularly useful for the treatment of autoimmune diseases where inhibition of biological activity of TNFα is important to disease pathology: e.g., arthritis, psoriatic arthritis, psoriasis, Crohn's disease, inflammatory bowel disease, ankylosing spondylitis, Sjögren's syndrome, Still's disease (macrophage activation syndrome), uveitis, scleroderma, myositis, Reiter's syndrome, and Wegener's syndrome. It is a preferred embodiment of this invention, these compounds may mimic the activity of bacterial protein A thereby facilitating the clearance of immune complexes. In any case, it is not intended that the scope of the present invention be limited by the mechanism by which an improvement in any inflammatory condition indicative of an autoimmune disease occurs. Indeed, an improvement in an autoimmune condition may occur by use of compounds of this invention by a poorly defined or unknown mechanism, but said improvement being determined by in vivo activity displayed in an appropriate animal model. Therefore, the mechanism(s) by which compound efficacy occurs is not an important nor limiting aspect of this invention. Important, however, is the fact the compounds of this invention exhibit limited toxicity such that they may be administered accordingly for the treatment of chronic autoimmune disease.

Compounds of the present invention include all pharmaceutically acceptable derivatives, such as salts and prodrug forms thereof, and analogues as well as any geometrical isomers or enantiomers. Formulations of the active compound may be prepared so as to provide a pharmaceutical composition in a form suitable for enteral, mucosal (including sublingual, pulmonary, and rectal); parenteral (including intramuscular, intradermal, subcutaneous, and intravenous); or topical (including ointments, creams, and lotions) administration. In particular, compounds of the present invention may be solubilized in an alcohol or polyol solvent (e.g., Solutol HS 15™ (polyethylene glycol 660 hydroxystearate from BASF), glycerol, ethanol, etc.) or any other biocompatible solvent such as dimethyl sulfoxide (DMSO) or Cremophor EL™ (also from BASF). The formulation may, where appropriate, be conveniently presented in discrete dosage units and may be prepared by any of the methods well-known in the art of pharmaceutical formulation. All methods include the step of bringing together the active pharmaceutical ingredient with liquid carriers or finely divided solid carriers or both as the need dictates. When appropriate, the above-described formulations may be adapted so as to provide sustained release of the active pharmaceutical ingredient. Sustained release formulations well-known to the art include the use of a bolus injection, continuous infusion, biocompatible polymers, or liposomes.

Suitable choices in amounts and timing of doses, formulation, and routes of administration can be made with the goals of achieving a favorable response in the mammal (i.e., efficacy), and avoiding undue toxicity or other harm thereto (i.e., safety). Therefore, "effective" refers to such choices that involve routine manipulation of conditions to achieve a desired effect: e.g., reducing or otherwise ameliorating tissue injury associated with an immune response to body constituents (organs and tissues like adrenal, eye, joint, kidney, liver, lung, pancreas, nervous system, skin, thyroid, etc.); restoring the immunological status or normalizing a pathological disorder/condition of the mammal (antibody titer, immune cell subsets, signaling by cytokines or chemokines, antibody-antigen immune complexes, etc.); removal of free antibodies and/or antibody-antigen immune complexes from the circulation; laboratory indicia of autoimmune disease (concentration or absolute amount of soluble mediators of inflammation, presence of autoantibodies, cellular proliferation, etc.); and combinations thereof. In particular, deleterious effects of conventional anti-TNFα treatment may be avoided.

The amount of compound administered is dependent upon factors such as, for example, bioactivity and bioavailability of the compound (e.g., half-life in the body, stability, and metabolism); chemical properties of the compound (e.g., molecular weight, hydrophobicity, and solubility); route and scheduling of administration; and the like. It will also be understood that the specific dose level to be achieved for any particular patient may depend on a variety of factors, including age, health, medical history, weight, combination with one or more other drugs, and severity of disease.

The term "treatment" or "treating" refers to, inter alia, reducing or alleviating one or more symptoms of autoimmune disease in a mammal (e.g., human) affected by disease or at risk for developing disease. For a given patient, improvement in a symptom, its worsening, regression, or progression may be determined by an objective or subjective measure. Treatment may also involve combination with other existing modes of treatment and agents (e.g., anti-inflammatory drugs, agents binding TNFα like antibody or soluble receptor, NSAIDs, corticosteroids, DMARDs). Thus, combination treatment may be practiced. In such embodiments, it is preferred that toxicity of chronic treatment or the additional agent is at least reduced or avoided by reducing the amount or concentration of the additional agent used in comparison to treatment without a compound of the present invention while obtaining a substantially equivalent effect on the patient.

It will be appreciated by those skilled in the art that the reference herein to treatment extends to prophylaxis as well as therapy of established or chronic autoimmune disease. It will be further appreciated that the amount of a compound of the invention required for treatment will vary not only with the particular compound used for treatment but also with the route of administration, the nature of the autoimmune condition being treated and the age and general health of the patient. The dose to be administered will ultimately be at the discretion of the physician. In general, however, the dose will be in the range from about 0.1 to about 200 mg/kg of body weight per day. Preferably, doses will range from about 1 to about 100 mg/kg per day. More preferably, the range will be between 2 to 50 mg/kg per day. The dosage unit per day may be 10 mg or more, 100 mg or more, 10 g or less, 40 g or less, or any range therebetween.

Finally, and where appropriate, compounds of the present invention may be used in combination with other treatments for autoimmune disease well-known to the art. Other prior art treatments include those described above as represented by nonsteroidal anti-inflammatory drugs (NSAIDs) (e.g., ibuprofen, aspirin, naproxen, etodolac, and ketoprofen); corticosteroids (e.g., hydrocortisone, pregnisone, and dexamethasone); disease-modifying anti-rheumatic drugs (DMARDs) (e.g., cytotoxic drugs like methotrexate or azathioprine, immunosuppressants like cyclosporin or FK506, hydrochloroquine, organogold salts) and biologicals. The individual components of such combinations may be administered either sequentially or simultaneously in separate or combined pharmaceutical formulations. Alternatively, new pharmaceutical formulations may be created to accommodate the combination of compounds of this invention with conventional treatments for autoimmune disease.

Compounds of the present invention may also be used as affinity agents to bind antibody (e.g., human isotypes like IgM, IgD, IgA1, IgA2, IgE, IgG1, IgG2, IgG3, and/or IgG4). Free (i.e., not bound to antigen) antibody and/or antibody-antigen immune complex may be specifically bound by such affinity agents. Large affinity complexes may be isolated by selective precipitation or differential centrifugation, or identified by flocculation assays. But it is preferred to immobilize one or more compounds to an insoluble support material (e.g., agarose, dextran, cellulose, polyacrylamide, other polymeric materials, silica, and glass) preferably covalently linked directly or indirectly by a linker. A compound of the present invention may be synthesized in situ on the support or through an activated organic linker. Optionally, the linker may be cleavable (e.g., by a reducing agent or site-specific protease) such that the compound (with or without bound antibody) may be detached from the support. For example, one or more compounds of the present invention may be covalently linked to a support in the form of a glass slide, multiwell plate, optical fiber, protein chip or test tube for assays and analysis; tissue culture dish for incubating cells or antigen; and magnetic beads, porous membrane or chromatographic media for separation. Antibody or other Fc-containing material may be bound to one or more compounds of the present invention (i.e., isolation), and then optionally separated from unbound material (with or without washing and multiple rounds of binding under different conditions) to purify Fc-containing material. For example, ionic strength (e.g., salt concentration) or pH may change binding conditions and be used to release Fc-containing material.

EXAMPLES

The following examples further illustrate the practice of this invention but are not intended to be limiting thereof.

The general synthetic sequence for preparation of the compounds useful in the present invention is outlined in schemes 1 and 2. Scheme 1 illustrates the synthetic route employed for the disubstituted purine derivatives while scheme 2 illustrates the synthetic method for the trisubstituted purine derivatives described in this invention.

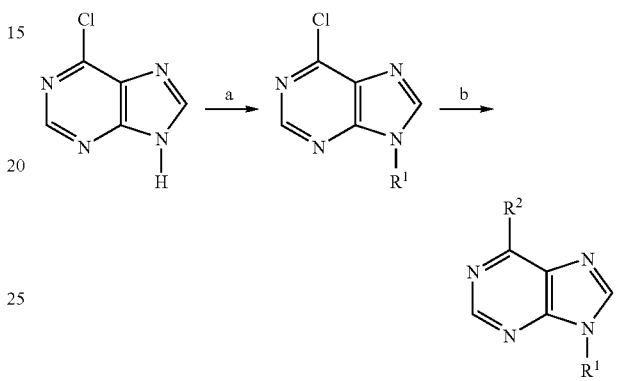

Reagents: (a) aralkyl alcohol, DEAD, Ph$_3$P, THF; (b) aralkylamine, DIEA, n-butanol.

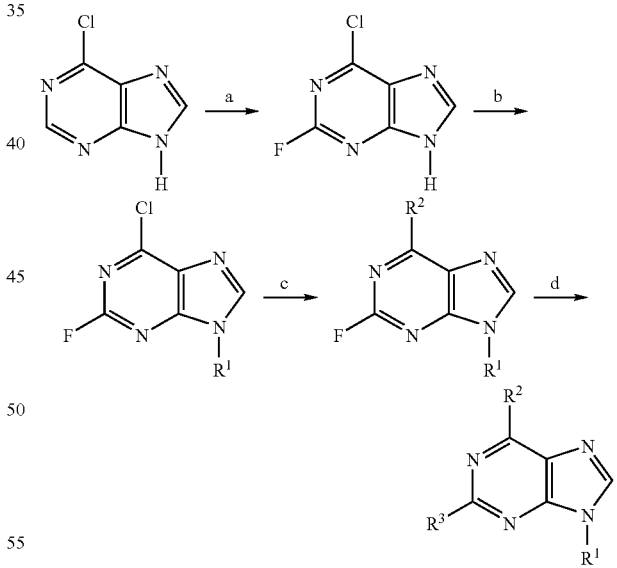

Reagents: (a) NaNO$_2$, HBF$_4$ (48%); (b) aralkyl alcohol, DEAD, Ph$_3$P, THF; (c) aralkylamine, DIEA, n-butanol; (d) ammonia or alkylamine or alkyl alcohol or alkyl thiol, DIEA, n-butanol.

Instrumentation:

All HPLC chromatograms and mass spectra were recorded on a HP 1100 LC-MS Agilent instrument using a diode array detector. Analysis was performed by one of the following four methods: an analytical C18 column (75×4.6 mm, 5 microns) with a gradient of 1% to 40% acetonitrile-water containing 0.01% TFA in 6 min and a flow of 2 mL/min (method 1) or an analytical C18 column (75×4.6 mm, 5 microns) with a gradient of 10% to 99% acetonitrile-water containing 0.01% TFA in 6 min and a flow of 2 mL/min (method 2) or an analytical C18 column (75×4.6 mm, 5 microns) with a gradient of 15% to 99% acetonitrile-water containing 0.01% TFA in 6 min and a flow of 2 mL/min (method 3), or an analytical C18 column (75×4.6 mm, 5 microns) with a gradient of 1% to 20% acetonitrile-water containing 0.01% TFA in 6 min and a flow of 2 mL/min (method 4).

Example 1

(Representative Example of Scheme 1): Synthesis of N-{9-[2-(4-aminophenyl)ethyl]-9H-purin-6-yl}benzene-1,3-diamine dihydrochloride (compound 1)

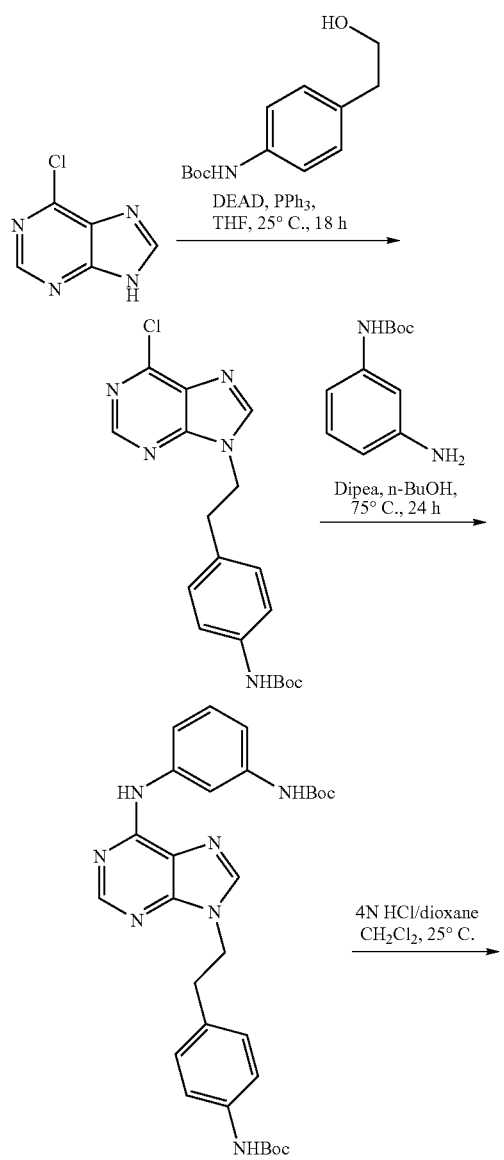

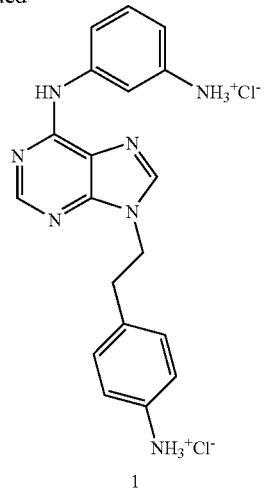

To a solution of 4-aminophenethyl alcohol (3.0 g, 21.8 mmol) in tetrahydrofuran (100 mL) at room temperature was added di-tert-butyldicarbonate (5.2 g, 23.6 mmol) and triethylamine (4.7 mL, 32.8 mmol). The reaction was stirred for 16 h at room temperature. The solution was diluted with water (100 mL) and ethyl acetate (100 mL). The aqueous layer was extracted with ethyl acetate (100 mL). The organic layers were dried over sodium sulfate and filtered. The protected amine was obtained as a white solid (4.3 g, 83%). This compound (1.7 g, 7.4 mmol) and triphenylphosphine (1.9 g, 7.4 mmol) were added to a suspension of 6-chloropurine (761 mg, 4.9 mmol) in dry tetrahydrofuran (13 mL) at room temperature. The resulting mixture was evaporated to dryness. Dry tetrahydrofuran (13 mL) was added and the suspension was cooled to 0° C. followed by dropwise addition of diethylazo-dicarboxylate (891 µL, 5.7 mmol). After 16 h reaction at room temperature, the solution was concentrated under reduced pressure. The crude residue was purified on a Biotage™ 25M column (silica, hexane/AcOEt 95:5 to 65:35) to yield N-9 alkylated purine as a white solid (1.8 g, quantitative).

To a suspension of 1,3-phenylenediamine (8.2 g; 75.4 mmol) in methylene chloride (21 mL) at room temperature was added dropwise over one hour a solution of di-tert-butyldicarbonate (2.7 g, 12.6 mmol) in methylene chloride (130 mL). The solution was then stirred overnight at room temperature. After 18 h reaction, the solution was evaporated to dryness under reduced pressure. The residual oil was dissolved in ethyl acetate (50 mL) and washed with 2N sodium carbonate (50 mL). The aqueous layer was extracted with ethyl acetate (2×50 mL). The combined organic layers were washed with brine (50 mL), dried over sodium sulfate, filtered, and evaporated to dryness. The crude residue was purified on a BIOTAGE™ 40S column (silica, hexane/AcOEt 95:5 to 1:1) to yield N-1-tert-butyloxycarbonyl-1,3-phenylene-diamine as a white solid (2.4 g, 93%). This compound (40 mg, 0.2 mmol) and diisopropylethylamine (50 µL, 0.3 mmol) were added to a solution of 6-chloro-N-9-alkylated purine (35 mg, 0.1 mmol) in n-butanol (2.0 mL) at room temperature. After 48 h reaction at 90° C., the brown solution was concentrated under reduced pressure. The crude residue was purified on a BIOTAGE™ 12M column (silica, hexane/AcOEt 6:4 to AcOEt/MeOH 8:2) to yield the disubstituted purine as a brown solid (32 mg, 63%). To a solution of this material (32 mg, 0.06 mmol) in dichloromethane (2.0 mL) at room temperature was added a solution of 4N HCl in dioxane (2.0 mL). After 3 h reaction at 25° C., the solution was concentrated under reduced pressure and dried for 16 h under vacuum to yield compound 1 as a pale brown solid. Yield of product: 23 mg (94%); $R_f$=0.4 (AcOEt/MeOH 95:5); $^1$H NMR (400 MHz, CD$_3$OD): δ 8.50 (s, 1H), 8.30 (s, 1H), 8.17 (t, 1H), 8.80-8.70 (m, 1H), 7.58 (t, 1H), 7.40-7.20 (m, 5H), 4.63 (t, 2H), 3.31 (t, 2H); LRMS (ESI): m/z 346 (MH$^+$), 368 (M+Na); HPLC (method 1): 2.5 min.

Example 2

(Representative Example of Scheme 2): Synthesis of N6-(3-Amino-phenyl)-9-[2-(4-amino-phenyl)-ethyl]-N2-cyclopropylmethyl-9H-purine-2,6-diamine (Compound 3)

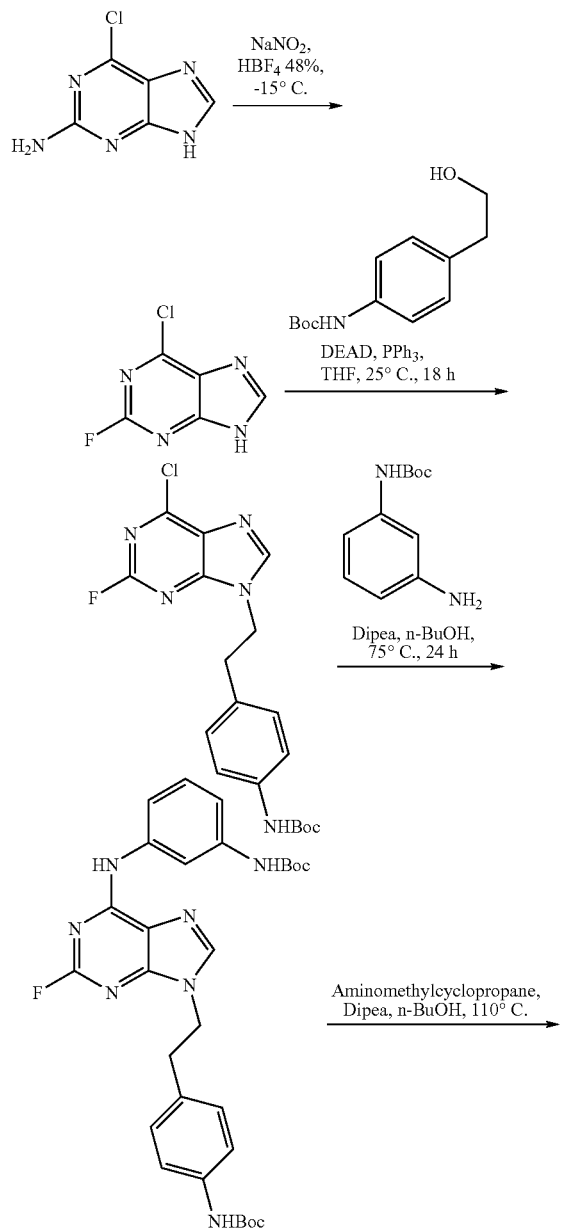

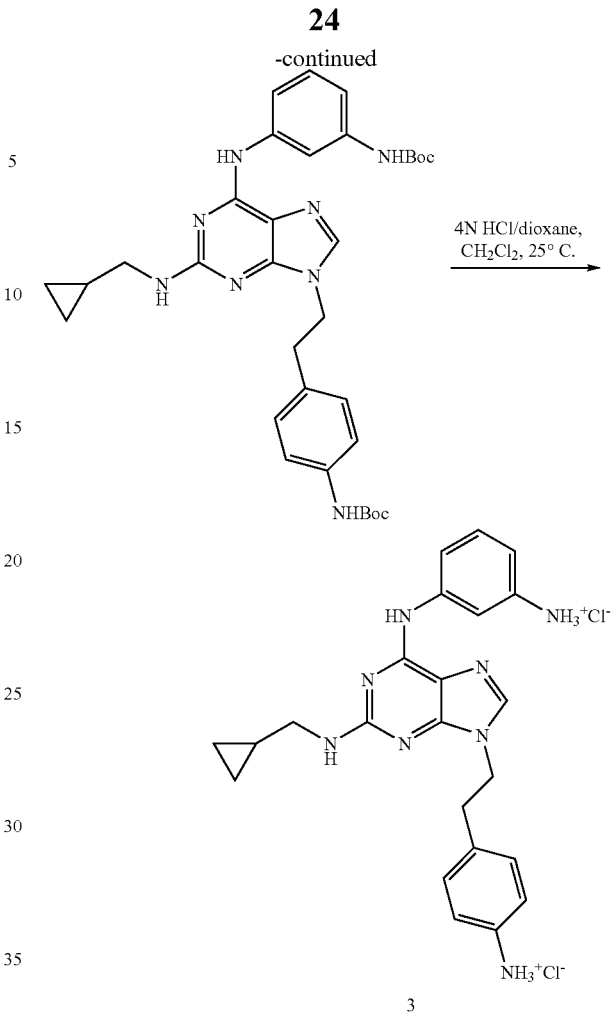

To 2-amino-6-chloropurine (5.0 g, 29.5 mmol) in a solution of tetrafluoroboric acid in water (100 mL) at −15° C. was added dropwise sodium nitrite (3.5 g, 50 mmol) in water (160 mL) over a period of 1.5 h. After 20 min at room temperature, the pH of the solution was adjusted to 6 with 50% aqueous sodium hydroxide. The solution was concentrated under reduced pressure. The crude residue was purified on a BIOTAGE™ 40S column (silica, CH$_2$Cl$_2$/MeOH 9:1) to give 2-fluoro-6-chloropurine (2.3 g, 52%). This compound (1.5 g, 8.6 mmol) was suspended in dry tetrahydrofuran (20 mL) at 25° C. The 4-(N-1-tert-butyloxycarbonyl)-aminophenethyl alcohol (3.4 g, 14.5 mmol) and triphenylphosphine (3.8 g, 14.5 mmol) were then added, and the mixture evaporated to dryness. Dry tetrahydrofuran (20 mL) was added and the suspension was cooled to 0° C. before dropwise addition of diethylazodicarboxylate (1.5 mL, 9.8 mmol). After 16 h reaction at room temperature, the solution was concentrated under reduced pressure. The crude residue was purified on a BIOTAGE™ 25M column (silica, hexane/AcOEt 95:5 to 75:25) to yield N-9 alkylated purine as a white solid (2.9 g, 87%). To a solution of alkylated 2-fluoro-6-chloropurine (3.0 g, 7.7 mmol) in n-butanol (15 mL) at 25° C. was added N-1-tert-butyloxycarbonyl-1,3-phenylenediamine (1.8 g, 8.8 mmol) and diisopropylethylamine (2.7 mL, 15.3 mmol). After 48 h reaction at 65° C., the brown solution was concentrated under reduced pressure. The crude residue was purified on a BIOTAGE™ 40M column (silica, hexane/AcOEt 65:45 to 0:1) to yield the fluoropurine derivative as a brown solid (2.8 g, 63%). To a solution of this product (2.8 g, 4.9 mmol) in n-butanol (15 mL) at room temperature was added aminomethylcyclopropane (1.2 g, 17.1 mmol) and diisopropylethylamine (1.7 mL, 9.8 mmol). After 48 h reaction at 110° C., the brown solution was concentrated under reduced pressure. The crude residue was purified on a BIOTAGE™ 40M column (silica, hexane/AcOEt 60:40 to AcOEt/MeOH 98:2) to yield the protected trisubstituted purine as a white solid (2.3 g, 73%). To a solution of this compound (2.08 g, 3.38 mmol) in dichloromethane (10 mL) at room temperature was added 4N HCl in dioxane (10 mL). The reaction was stirred for 5 h at 25° C. and the solution was concentrated under reduced pressure. The solid was then dried for 16 h under vacuum to yield compound 3 as a brown solid. Yield of product: 1.4 g (quantitative); $R_f$=0.1 ($CH_2Cl_2$/MeOH 98:2); $^1$H NMR (400 MHz, $CD_3OD$): δ 8.24 (s, 1H), 8.20-7.60 (m, 2H), 7.60-7.00 (m, 6H), 4.56 (t, 2H, J=7.0 Hz), 3.40-3.20 (m, 4H), 1.25-1.15 (m, 1H), 0.60-0.50 (m, 2H), 0.40-0.20 (m, 2H); LRMS (ESI): m/z 415 ($MH^+$), 437 (M+Na); HPLC (method 2): 1.6 min.

Example 3

N6-(3-Amino-phenyl)-9-[2-(4-amino-phenyl)-ethyl]-9H-purine-2,6-diamine (Compound 2)

The above compound was prepared as in Example 1 starting with 2-amino-6-chloropurine. Brown solid; $^1$H NMR (400 MHz, $CD_3OD$): δ 7.92 (s, 2H), 7.63 (d, 1H, J=8.8 Hz), 7.46 (t, 1H, J=7.6 Hz), 7.40-7.20 (m, 4H), 7.00 (d, 1H, J=8.2 Hz), 4.44 (t, 2H, J=7.2 Hz), 3.24 (t, 2H, J=6.8 Hz); LRMS (ESI): m/z 361 ($MH^+$), 383 (M+Na); HPLC (method 3): 0.4 min.

Example 4

6-{6-(3-Amino-phenylamino)-9-[2-(4-amino-phenyl)-ethyl]-9H-purin-2-ylamino}-hexan-1-ol (Compound 4)

The above compound was prepared as in Example 2 except 6-aminohexanol replaced aminomethylcyclopropane. Brown solid; $^1$H NMR (400 MHz, $CD_3OD$): δ 8.00-7.60 (m, 3H), 7.46 (t, 1H, J=8.2 Hz), 7.40-7.20 (m, 4H), 7.10-7.00 (m, 1H), 4.46 (t, 2H, J=7.0 Hz), 3.54 (t, 2H, J=6.5 Hz), 3.48 (t, 2H, J=7.0 Hz), 3.26 (t, 2H, J=7.0 Hz), 1.80-1.50 (m, 2H), 1.50-1.30 (m, 4H); LRMS (ESI): m/z 461 ($MH^+$); HPLC (method 2): 1.4 min.

Example 5

N6-(3-Amino-phenyl)-9-[2-(4-amino-phenyl)-ethyl]-N2-cyclopropyl-9H-purine-2,6-diamine (Compound 5)

The above compound was prepared as in Example 2 except cyclopropylamine replaced aminomethylcyclopropane. Brown solid; $^1$H NMR (400 MHz, $CD_3OD$): δ 8.00-7.90 (m, 1H), 7.90-7.80 (m, 2H), 7.50-7.20 (m, 5H), 7.10-6.95 (m, 1H), 4.47 (t, 2H, J=7.0 Hz), 3.30-3.20 (m, 2H), 2.90-2.80 (m, 1H), 0.90-0.80 (m, 2H), 0.70-0.50 (m, 2H); LRMS (ESI): m/z 401 ($MH^+$); HPLC (method 2): 1.3 min.

Example 6

N6-(3-Amino-phenyl)-9-[2-(4-amino-phenyl)-ethyl]-N2-tert-butyl-9H-purine-2,6-diamine (Compound 6)

The above compound was prepared as in Example 2 except by tert-butylamine replaced aminomethylcyclopropane. Brown solid; $^1$H NMR (400 MHz, $CD_3OD$): δ 7.90 (s, 1H), 7.60 (s, 1H), 7.50-7.20 (m, 6H), 7.00 (d, 1H, J=7.0 Hz), 4.45 (t, 2H, J=7.0 Hz), 3.27 (t, 2H, J=7.0 Hz), 1.50 (s, 9H); LRMS (ESI): m/z 417 ($MH^+$), 439 (M+Na); HPLC (method 2): 1.8 min.

Example 7

N-[9-(4-Amino-benzyl)-9H-purin-6-yl]-benzene-1,3-diamine (Compound 7)

The above compound was prepared as in Example 1 except 4-nitrobenzyl bromide and potassium carbonate replaced 4-(N-1-tert-butyloxycarbonyl)-aminophenethylalcohol. The reduction of the nitro group was undertaken with 10% Pd/C and ammonium formate. Brown solid; $^1$H NMR (400 MHz, $CD_3OD$): δ 8.75 (s, 1H), 8.53 (s, 1H), 7.98 (s, 1H), 7.80-7.20 (m, 7H), 5.66 (s, 2H); LRMS (ESI): m/z 332 ($MH^+$), 354 (M+Na); HPLC (method 4): 3.6 min.

Example 8

2-{6-(3-Amino-phenylamino)-9-[2-(4-amino-phenyl)-ethyl]-9H-purin-2-ylamino}-ethanol (Compound 8)

The above compound was prepared as in Example 2 except 2-aminoethanol replaced aminomethylcyclopropane. Brown solid; $^1$H NMR (400 MHz, $CD_3OD$): δ 8.02 (s, 1H), 7.83 (s, 1H), 7.62 (d, 1H, J=8.2 Hz), 7.45 (t, 1H, J=8.2 Hz), 7.40-7.20 (m, 4H), 7.02 (d, 1H, J=6.3 Hz), 4.44 (t,2H, J=7.0 Hz), 3.78 (t, 2H, J=6.1 Hz), 3.60 (t, 2H, J=5.9 Hz), 3.25 (t, 2H, J=6.8 Hz); LRMS (ESI): m/z 405 ($MH^+$); HPLC (method 1): 2.5 min.

Example 9

N-{9-[2-(4-Benzyloxy-phenyl)-ethyl]-2-fluoro-9H-purin-6-yl}-benzene-1,3-diamine (Compound 9)

The above compound was prepared as in Example 1 starting with 2-fluoro-6-chloropurine. Brown solid; $^1$H NMR (400 MHz, $CD_3OD$): δ 8.52 (s, 1H), 8.30 (t, 1H, J=1.9 Hz), 7.90-7.70 (m, 1H), 7.57 (t, 1H, J=8.0 Hz), 7.40-7.15 (m, 6H), 7.03 (d, 2H, J=8.8 Hz), 6.90 (d, 2H, J=8.8 Hz), 5.03 (s, 2H), 4.55 (t, 2H, J=7.0 Hz), 3.15 (t, 2H, J=7.0 Hz); LRMS (ESI): m/z 455 ($MH^+$), 477 (M+Na); HPLC (method 2): 3.5 min.

Example 10

N6-(3-Amino-phenyl)-9-[2-(4-amino-phenyl)-ethyl]-N2-(2,2-dimethyl-propyl)-9H-purine-2,6-diamine (Compound 10)

The above compound was prepared as in Example 2 except neopentylamine replaced aminomethylcyclopropane. Brown solid; $^1$H NMR (400 MHz, $CD_3OD$): δ 8.05 (s, 1H), 7.77 (s, 2H), 7.52 (t, 1H, J=8.2 Hz), 7.45-7.20 (m, 4H), 7.15 (d, 1H, J=6.8 Hz), 4.50 (t, 2H, J=7.0 Hz), 3.40-3.20 (m, 4H), 0.99 (s, 9H); LRMS (ESI): m/z 431 ($MH^+$), 453 (M+Na); HPLC (method 2): 1.9 min.

Example 11

N6-(3-Amino-phenyl)-9-[2-(4-amino-phenyl)-ethyl]-N2-isobutyl-9H-purine-2,6-diamine (Compound 11)

The above compound was prepared as in Example 2 except isobutylamine replaced aminomethylcyclopropane. Brown solid; ¹H NMR (400 MHz, CD₃OD): δ 8.45 (s, 1H), 8.20-7.90 (m, 2H), 7.56 (t, 1H, J=8.2 Hz), 7.50-7.00 (m, 5H), 4.59 (t, 2H, J=7.0 Hz), 3.40-3.20 (m, 2H), 2.00 (h, 1H, J=6.8 Hz), 1.01 (d, 6H, J=6.6 Hz); LRMS (ESI): m/z 417 (MH⁺), 439 (M+Na); HPLC (method 2): 1.7 min.

Example 12

N-{9-[2-(3-Amino-phenyl)-ethyl]-9H-purin-6-yl}-benzene-1,3-diamine (Compound 12)

The above compound was prepared as in Example 1 except 3-nitrophenethylalcohol replaced 4-(N-1-tert-butyloxycarbonyl)-aminophenethylalcohol. The reduction of the nitro group was undertaken using 10% Pd/C and ammonium formate. Brown solid; ¹H NMR (400 MHz, CD₃OD): δ 8.45 (s, 1H), 8.40-8.20 (m, 1H), 8.20-8.00 (m, 1H), 7.71 (d, 1H, J=8.2 Hz), 7.51 (t, 1H, J=8.0 Hz), 7.41 (t, 1H, J=7.8 Hz), 7.35-7.00 (m, 4H), 4.59 ( t, 2H, J=7.0 Hz), 3.40-3.20 (m, 2H); LRMS (ESI): m/z 346 (MH⁺), 368 (M+Na); HPLC (method 2): 2.5 min.

Example 13

N6-(3-Amino-phenyl)-9-[2-(4-amino-phenyl)-ethyl]-N2-cyclopentyl-9H-purine-2,6-diamine (Compound 13)

The above compound was prepared as in Example 2 except cyclopentylamine replaced aminomethylcyclopropane. Brown solid; ¹H NMR (400 MHz, CD₃OD): δ 8.45 (s, 1H), 8.13 (s, 1H), 8.00-7.80 (m, 1H), 7.57 (t, 1H, J=8.2 Hz), 7.50-7.30 (m, 4H), 7.30-7.10 (m, 1H), 4.57 (t, 2H, J=7.0 Hz), 4.35 (q, 1H, J=6.6 Hz), 3.40-3.20 (m, 2H), 2.20-2.00 (m, 2H), 1.90-1.60 (m, 6H); LRMS (ESI): m/z 429 (MH⁺), 451 (M+Na); HPLC (method 2): 1.7 min.

Example 14

N-{9-[2-(4-Fluoro-phenyl)-ethyl]-9H-purin-6-yl}-benzene-1,3-diamine (Compound 14)

The above compound was prepared as in Example 1 except 4-fluorophenethylalcohol replaced 4 (N-1-tert-butyloxycarbonyl) phenethylalcohol. Brown solid; ¹H NMR (400 MHz, CD₃OD): δ 8.47 (s, 1H), 8.30-8.20 (m, 1H), 8.07 (s, 1H), 7.80-7.60 (m,1H), 7.51 (t, J=7.54 Hz, 1H), 7.20-7.00 (m, 3H), 7.00-6.80 (m, 2H), 4.53 (t, J=6.85 Hz, 2H), 3.19 (t, J=7.04 Hz, 2H); LRMS (ESI): m/z 349 (MH⁺), 371 (M+Na); HPLC (method 2): 2.2 min.

Example 15

Ability of Compounds to Mimic Protein A as Determined by Competitive Protein A binding ELISA As described above, this assay evaluates the ability of the exemplified compounds to mimic protein A. Such compounds can bind to the Fc portion of human IgG as ascertained by the inhibition of binding of protein A to human IgG. The competitive protein A binding ELISA assay was performed on a 96-well plate MAXISORP® surface to enhance the binding of protein A to the bottom of the plate. The wells were coated with 100 μL of protein A (0.8 μg) and incubated overnight at 4° C. After incubation, unbound protein A was removed by three washes with phosphate buffer saline (PBS). The plate was then incubated with 100 μL/well of a 2% solution of bovine serum albumin (BSA) for 1 h at 37° C. to block nonspecific protein binding. After incubation, the plate was washed three times with PBS. 50 μL of compound or protein A, diluted in PBS or PBS-20% DMSO at appropriate concentration, were added to the wells followed by addition of 50 μL of peroxidase-conjugated human IgG (HRP-IgG). After 1 h incubation at 37° C., the plate was washed three times with PBS to remove unbound HRP-IgG. Bound HRP-IgG was detected by incubation with 100 μL of 2,2'-azino-di [3-ethylbenzthiazoline sulfonate] diammonium salt crystals (ABTS) solution for 20 min in the dark at room temperature. The plate was then read at 405 nm on a BIO-TEK® EL 800 Universal Microplate Reader. Data was analyzed in a MICROSOFT® EXCEL® spreadsheet and the concentration of compound which inhibits 50% binding of protein A (IC₅₀) was calculated using PRISM® software, as shown in Table 1.

TABLE 1

IC₅₀ (μM) of protein A mimic compounds as ascertained by ELISA

| Compound No. | IC₅₀ (μM) Assay in PBS |
|---|---|
| 1 | 1.0 |
| 2 | 13 |
| 3 | 0.7 |
| 4 | 4.8 |
| 5 | 13 |
| 6 | 1.8 |
| 7 | 0.2 |
| 8 | 64 |
| 9 | 7.1 |
| 10 | 6.0 |
| 11 | 22 |
| 12 | 52 |
| 13 | 0.2 |
| 14 | 0.6 |

Example 16

Effect of Compounds on LPS-induced TNFα Production in Mouse J774A-1 Cell Line

The effect of compounds on TNFα production was measured by ELISA using J774-1 cells stimulated by lipopolysaccharide (LPS). J774-1 cells were cultured in the presence or absence of LPS and compound. Cells were cultured at 37° C. for 24 h and thereafter the supernatants were collected for the determination of the concentration of TNFα by ELISA as recommended by the manufacturer (BD Biosciences). Data was analyzed in a MICROSOFT® EXCEL® spreadsheet and the concentration of compound which inhibits 50% of TNFα production (IC₅₀) was calculated using PRISM® software, as shown in Table 2.

TABLE 2

Effect of Compounds on the Inhibition of TNFα Induced by LPS induction From J774A-1 Cells

| Compound No. | IC₅₀ (μM) |
|---|---|
| 1 | >100 |
| 2 | 76 |
| 3 | >50 |
| 4 | >50 |
| 5 | 9.2 |
| 6 | 2.3 |
| 7 | >100 |

TABLE 2-continued

Effect of Compounds on the Inhibition of TNFα Induced
by LPS induction From J774A-1 Cells

| Compound No. | IC$_{50}$ (µM) |
|---|---|
| 8 | 11 |
| 9 | >50 |
| 10 | 5.3 |
| 11 | 11 |
| 12 | >50 |
| 13 | 6.2 |
| 14 | >50 |

Example 17

Effect of Compound 1 on Oxazolone-Induced
Delayed-Type Hypersensitivity (DTH)

Compounds were tested for their ability to treat oxazolone-induced delayed-type hypersensitivity (DTH) in mice. On day 0, mice were sensitized with 100 µL of oxazolone in 5% acetone. On day 0, 1 and 2, mice were treated by intravenous administration of the vehicle (control) or methotrexate (MTX; positive control) or the compound at 50 mg/kg. Mice were challenged with an application of 50 µL of oxazolone on the surface of the right ear (first challenge, day 3; second challenge, day 10). Ear thickness was measured on day 4 to day 7, and on day 11 to 14. Redness and crust formation was also observed. Mice were sacrificed on day 14. T$_{DTH}$ (CD4) cells play an important role in regulating the intensity of the DTH response.

As shown in Table 3, compound 1 induces a significant reduction of the inflammation as seen by lower ear thickness. Compound 1 alone is equipotent to methotrexate. Compound 1 also reduces redness, crust formation, and ear swelling.

TABLE 3

Effect of intravenous administration of compound 1 on DTH

| | Inflammation/Ear thickness (mm) | | | |
|---|---|---|---|---|
| | Challenge 1 | | Challenge 2 | |
| Control | 0.29 ± 0.10 | | 0.83 ± 0.46 | |
| Methotrexate | 0.17 ± 0.04 | P = 0.001 | 0.46 ± 0.17 | P = 0.02 |
| Compound 1 | 0.19 ± 0.06 | P = 0.008 | 0.56 ± 0.12 | P = 0.05 |

The effect of oral administration of compound 1 was determined following the protocol described above with the exception that compound 1 was orally administered at 50 or 150 mg/kg from day 0 to day 13. The positive control was hydrocortisone. FIG. 1 shows the effect of compound 1 on DTH. Compound I induces a significant reduction of the inflammation as seen by lower ear thickness in both challenges 1 and 2.

Example 18

Effect of Compound 1 on Freund's
Adjuvant-Induced Arthritis (AIA)

AIA was induced in female Lewis rats by the injection of lyophilized *Mycobacterium butyricum* suspended in mineral oil into the footpad. The development of arthritis was monitored over a 3 week period post-adjuvant injection. Inflammation peaks at day 3 following the adjuvant administration. Immune activation appears around day 14. Compounds were injected i.v. day-3, -2 and -1 pre-adjuvant injection and at day 10, 11 and 12 post-adjuvant injection. Body weight was recorded. The arthritis index, which is a measure of inflammation (edema), redness, and stiffness of the articulations, was used to monitor the development of the disease. The degree of arthritis was determined by measuring two perpendicular diameters of the ankles in the mediolateral and dorsoventral planes using a caliper. Joint circumference in millimeters is then calculated using a geometric formula. Both the incidence and severity of the arthritis was evaluated. Incidence is defined as the number of rats with clinical evidence of joint inflammation during the study period.

Figure 2:
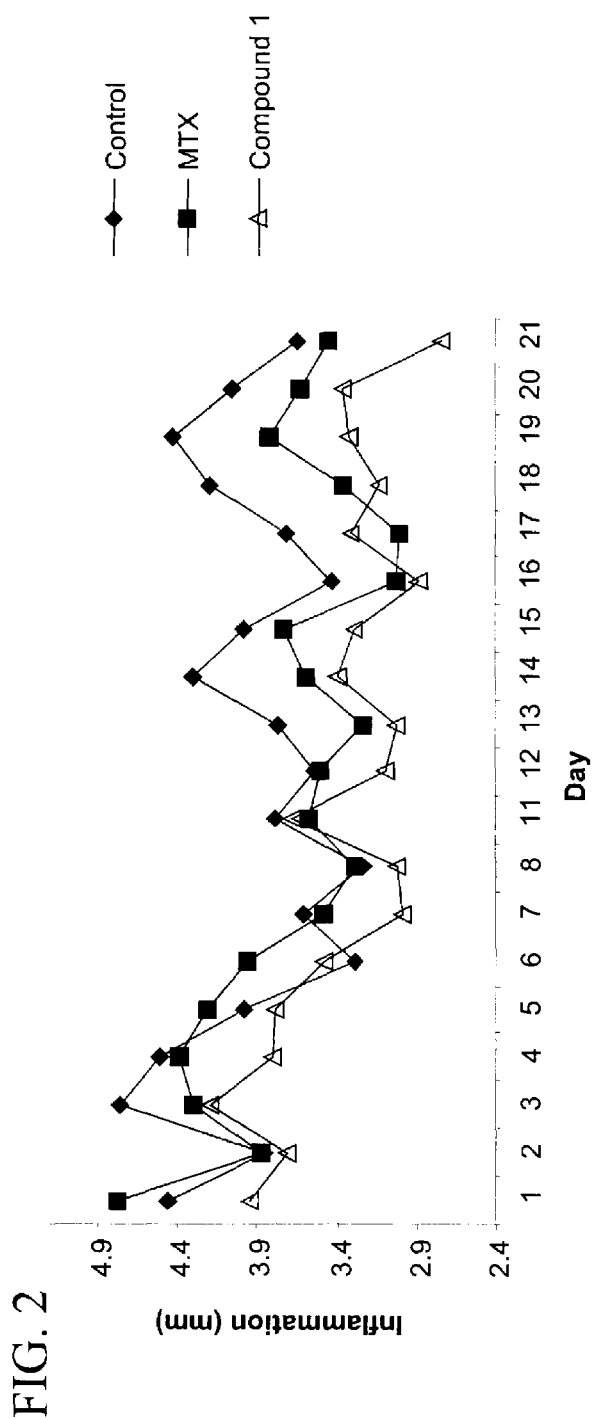
FIG. 2 shows the effect of intravenous administration of compound 1 as compared to methotrexate on adjuvant-induced arthritis.

As shown in FIG. 2, 100% of the animals rapidly developed a synovitis. A significant reduction (20%) in the severity of arthritis (inflammatory index) was observed by intravenous injection of methotrexate (positive control) by day 13 and over. A significant reduction (up to 25%) of the inflammatory index was also observed with compound 1 from day 1 to day 21.

Figure 3:
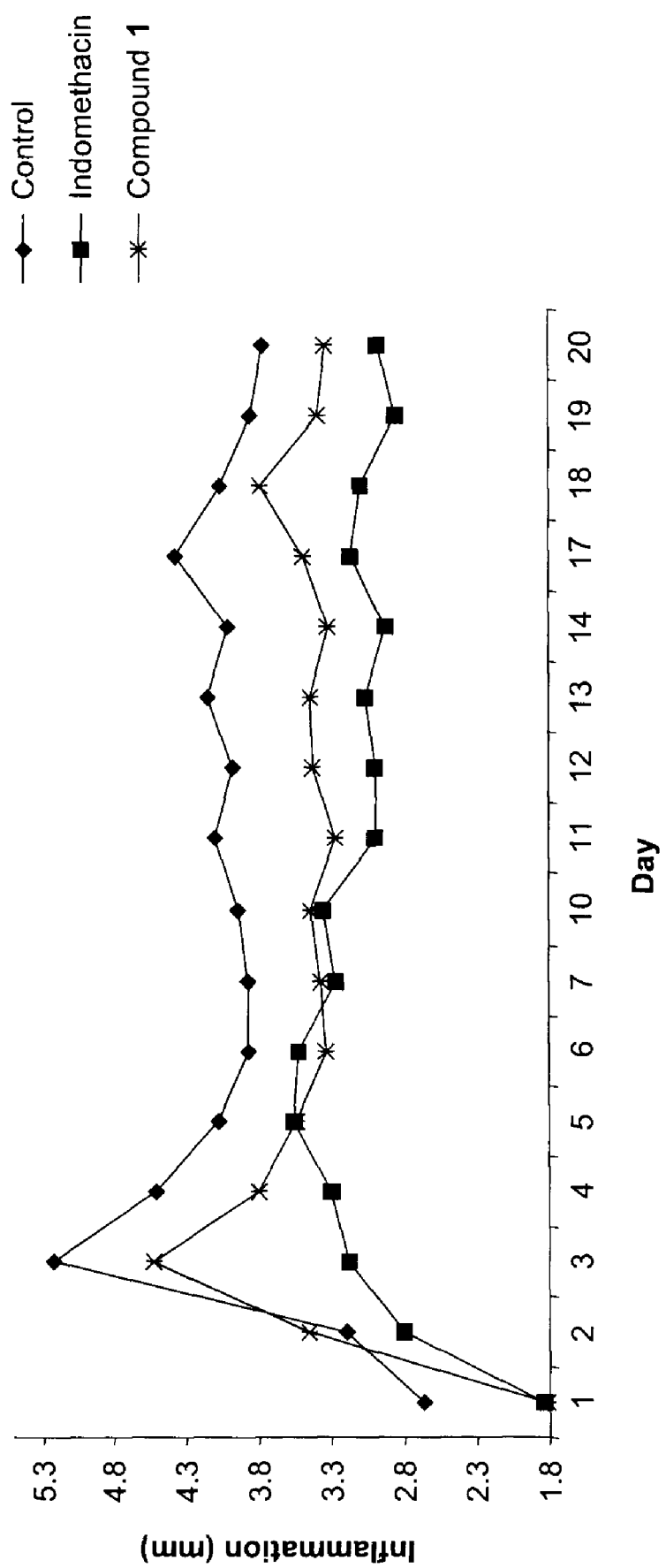
FIG. 3 shows the effect of oral administration of compound 1 as compared to indomethacin on adjuvant-induced arthritis.

The effect of oral administration of compound 1 was determined following the protocol described above with the exception that compound 1 was orally administered at 50 mg/kg from day-3 to day 19. The positive control was indomethacin. As shown in FIG. 3, a significant reduction (10-40%) in the severity of arthritis (inflammatory index) was observed by oral administration of indomethacin (positive control) by day 1 and over. A significant reduction (10-30%) of the inflammatory index was also observed with compound 1 from day 1 to day 20.

Patents, patent applications, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A compound of the following formula:

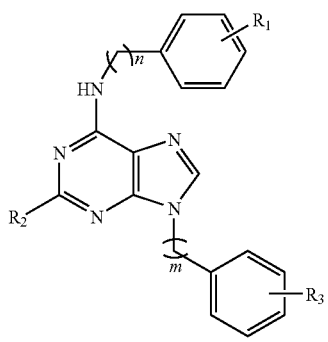

n = 0-2
m = 0-2
m is not necessarily equal to n;
where:
$R_1$ is $NH_2$;
$R_3$ is $NH_2$, F, or Cl; and
$R_2$ is H, F, Cl, $NH_2$, or NH—R—XH;

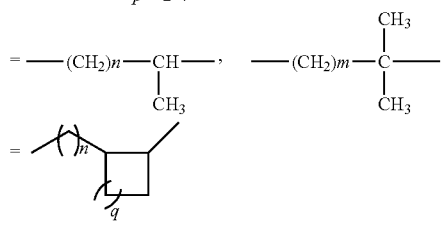

q = 0-3
X = $CH_2$, NH, O, or S or a pharmaceutically acceptable salt thereof.

2. The compound according to claim 1, wherein $R_1$=$NH_2$; $R_3$=$NH_2$, F, or Cl; n=0; and m=2.

3. The compound according to claim 1, wherein $R_1$=meta-$NH_2$; $R_3$=meta-$NH_2$, F, or Cl; $R_2$=H; n=0; and m=2.

4. A compound selected from the group consisting of:

| Compound No. | Structure |
|---|---|
| 1 | 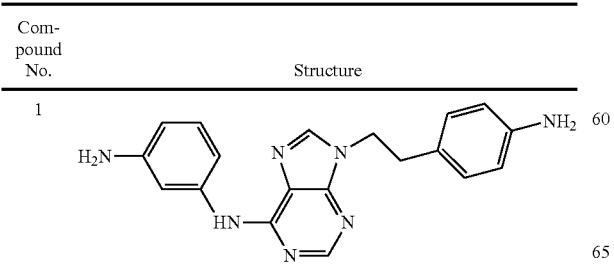 |
| 2 | 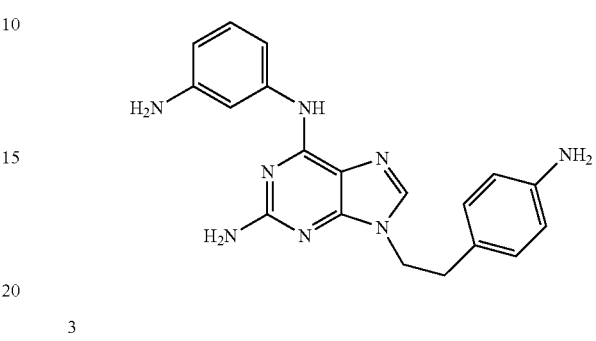 |
| 3 | 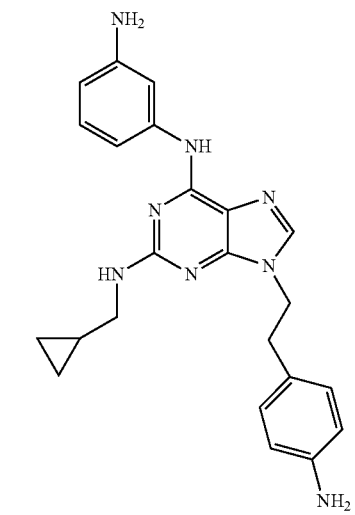 |
| 4 | 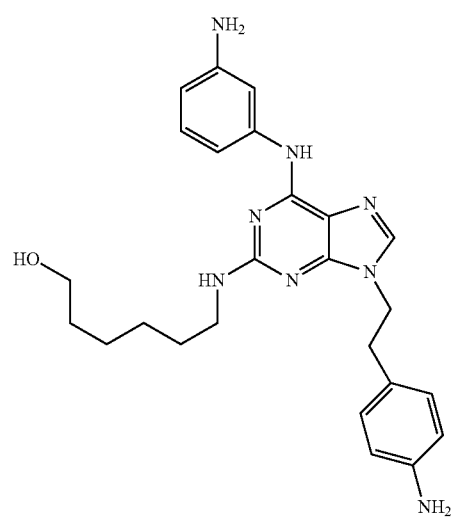 |

-continued
| Compound No. | Structure |
|---|---|
| 5 | 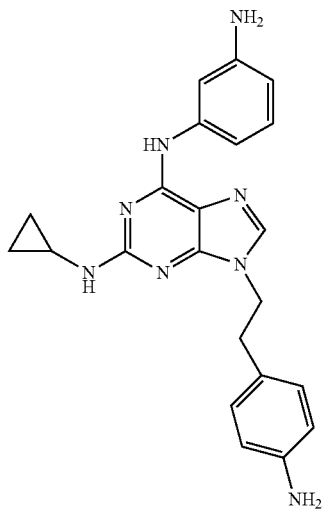 |
| 6 | 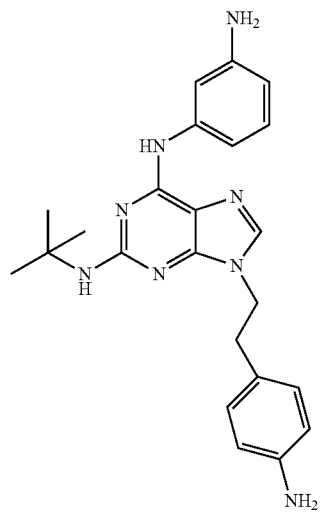 |
| 7 | 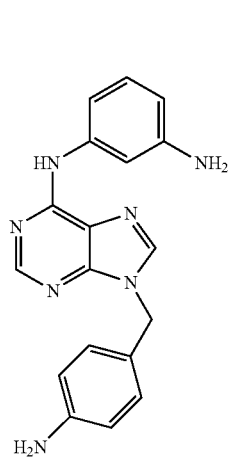 |
-continued
| Compound No. | Structure |
|---|---|
| 8 | 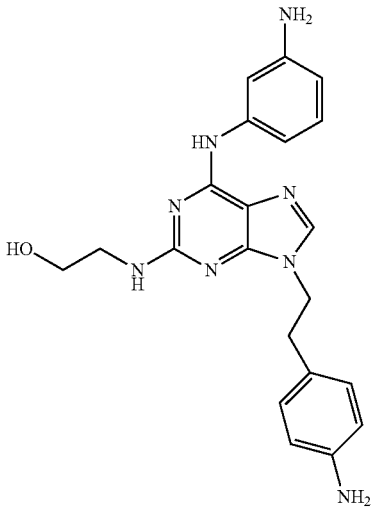 |
| 10 | 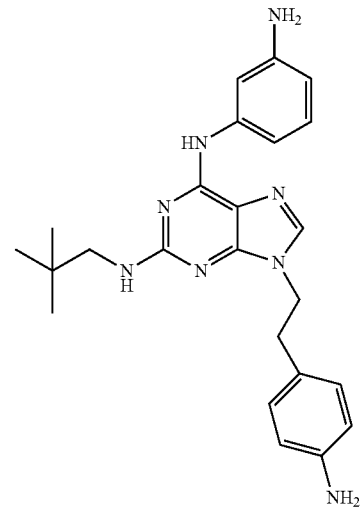 |
| 11 | 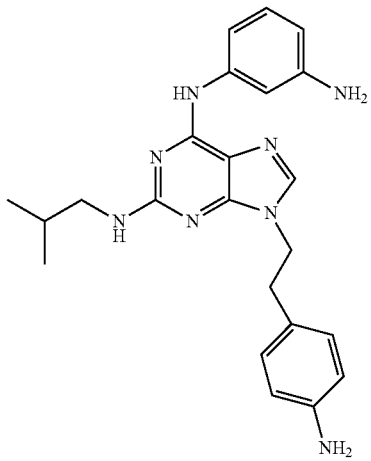 |

-continued

| Compound No. | Structure |
|---|---|
| 12 | 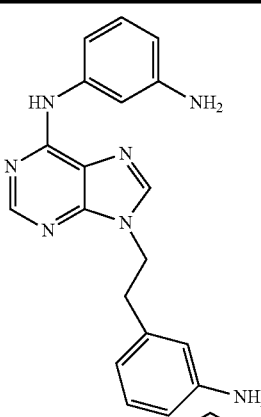 |
| 13 | 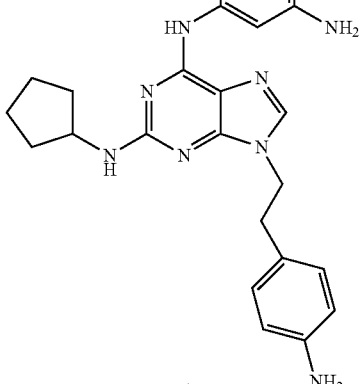 |
| and 14 | 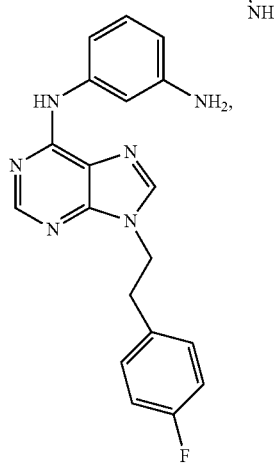 | or a pharmaceutically acceptable salt thereof.

5. The compound according to claim 1, wherein said compound is capable of noncovalently binding to the Fc portion of a human IgG antibody.

6. A composition comprising at least one compound according to claim 1 and a pharmaceutically acceptable carrier.

7. The composition according to claim 6 further comprising a recombinant protein which binds to human TNFα.

8. The composition according to claim 6 further comprising methotrexate, an anti-inflammatory corticosteroid, a non-steroidal anti-inflammatory drug, or a combination thereof.

9. A method for isolating an antibody or an antibody-antigen immune complex, comprising binding a compound of claim 1 to an antibody or an antibody-antigen immune complex and separating unbound material to isolate said antibody or antibody-antigen immune complex.

10. The method of claim 9, wherein said compound is immobilized to an insoluble support.

11. A method of reducing and/or alleviating synovitis in a patient with rheumatoid arthritis or psoriatic arthritis, comprising administering to said patient a therapeutically effective amount of a compound according to claim 1.

12. The method of claim 9, wherein the said compound is covalently linked to a support selected from the group consisting of a glass slide, a multiwell plate, an optical fiber, a protein chip, a test tube, a tissue culture dish, a magnetic beads, a porous membrane or a chromatographic media.

13. The method of claim 9, wherein said antibody is an IgM, an IgD, an IgA1, an IgA2, an IgE, an IgG1, an IgG2, an IgG3, an IgG4, and and/or an Fc-containing material.

14. The method of claim 10, wherein said insoluble support is made of a material selected from the group consisting of agarose, dextran, cellulose, polyacrylamide, silica, and glass.

15. A method of reducing and/or alleviating synovitis in a patient with systemic lupus erythematosus, comprising administering to said patient a therapeutically effective amount of a compound according to claim 1.

* * * * *